United States Patent
Hilaire et al.

(10) Patent No.: US 6,416,543 B1
(45) Date of Patent: Jul. 9, 2002

(54) EXPANDABLE STENT WITH VARIABLE THICKNESS

(75) Inventors: Pierre Hilaire, Paris; Viviane Payrou, Villejuif, both of (FR)

(73) Assignee: CathNet-Science S.A., Paris (FR)

(*) Notice: Subject to any disclaimer, the term of this patent is extended or adjusted under 35 U.S.C. 154(b) by 0 days.

(21) Appl. No.: 09/445,655

(22) PCT Filed: Jun. 17, 1998

(86) PCT No.: PCT/EP98/04003

§ 371 (c)(1),
(2), (4) Date: Mar. 6, 2000

(87) PCT Pub. No.: WO98/58600

PCT Pub. Date: Dec. 30, 1998

(30) Foreign Application Priority Data

Jun. 20, 1997 (FR) .......................................... 97 07694

(51) Int. Cl.$^7$ .................................................. A61F 2/06
(52) U.S. Cl. ...................................... 623/1.16; 623/1.15
(58) Field of Search ............................... 623/1.15, 1.16

(56) References Cited

U.S. PATENT DOCUMENTS

| | | | | |
|---|---|---|---|---|
| 5,697,971 A | * | 12/1997 | Fischell et al. ............ | 623/1.15 |
| 5,807,404 A | * | 9/1998 | Richter ....................... | 623/1.16 |
| 5,925,061 A | * | 7/1999 | Ogi et al. .................... | 623/1.2 |
| 6,027,526 A | * | 2/2000 | Limon et al. ............... | 623/1.15 |
| 6,203,569 B1 | * | 3/2001 | Wijay ......................... | 623/1.15 |
| 6,245,101 B1 | * | 6/2001 | Drasler et al. ............. | 623/1.15 |

* cited by examiner

Primary Examiner—Bruce Snow
Assistant Examiner—Brian Pellegrino
(74) Attorney, Agent, or Firm—Volpe and Koenig, P.C.

(57) ABSTRACT

An expandable tubular device is used as a stent for implantation in the lumen of a body duct, such as a blood vessel in particular, in order to ensure a passage therein, said device consisting of an assembly of tubular elements aligned along a common longitudinal axis and successively joined together in pairs by a plurality of linking members, each tubular element consisting of a strip forming a zigzag corrugation defining bent extreme portions which are successively connected together in pairs in opposite directions by rectilinear intermediate portions, the thickness (e) of said strip forming each of the above-mentions tubular elements (1), measured radially relative to said tubular element, being greater than the width 1 of this strip in said bent portions (2).

2 Claims, 2 Drawing Sheets

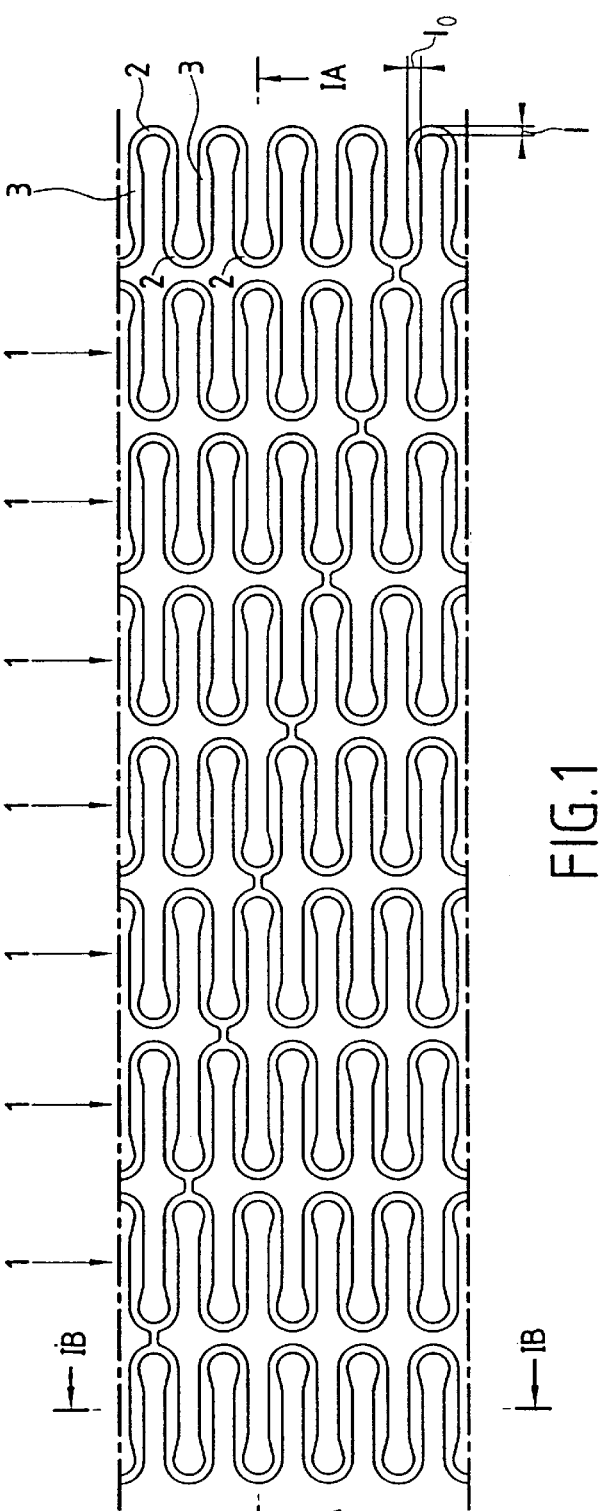
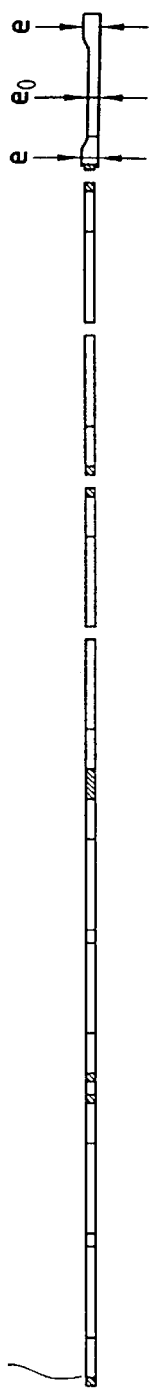

EXPANDABLE STENT WITH VARIABLE THICKNESS

The present invention relates in general terms to an expandable tubular device for implantation in the lumen of a body duct in order to ensure a passage therein.

BACKGROUND OF THE INVENTION

This invention applies mainly to the field of the treatment of blood vessels exhibiting stenoses, and more generally to the field of the treatment of diseases of various anatomical ducts of the human or animal body, such as, for example, the urinary ducts, especially the urethra, or else the digestive ducts, especially the esophagus.

The percutaneous implantation of an expandable tubular device, commonly designated by the American term stent, in a stenotic blood vessel is generally recommended, for example after a conventional angioplasty, for preventing the dilated vessel from closing up again spontaneously or for preventing its occlusion by the formation of a new atheromatous plaque and the possible recurrence of stenosis.

Document EP 0540290, in particular, discloses an expandable tubular device in the form of a stent; in general terms it consists of an assembly of radially expandable, tubular elements aligned along a common longitudinal axis and successively joined together in pairs by a plurality of linking members.

Each of the above-mentioned tubular elements consists of a strip forming a zigzag corrugation defining bent extreme portions which are successively connected together in pairs in opposite directions by rectilinear intermediate portions.

As can be seen, by virtue of this zigzag conformation, such a device is expandable between a first, constricted state, enabling it to be implanted percutaneously by means of an insertion device of reduced diameter, and a second, expanded state, in which said device makes it possible to ensure a passage in the lumen of the body duct.

The expandable device described in said document of the prior art is inserted by means of an angioplasty balloon-tip catheter.

For this purpose said device is placed in the constricted state on the balloon, the latter being inflated at the point of release in order to cause said device to dilate.

It has been observed that the expansion of the device described in the above-mentioned document does not occur uniformly, the symmetry of said device being in itself insufficient to distribute the deformation forces exerted thereon during the inflation of the balloon.

A particular consequence of the non-uniform expansion of the device described in the above-mentioned document, which is due especially to the absence of distribution of the radial forces exerted thereon, is that it does not allow a passage of constant dimensions to be obtained in the body duct, so this type of device is not entirely satisfactory.

Under these conditions the object of the present invention is to solve the technical problem consisting in the provision of a novel design of expandable tubular device which guarantees a uniform expansion, especially during the inflation of a balloon used to insert it, and a good distribution of the radial forces exerted thereon after its insertion, and which thus makes it possible to obtain a constant passage in the body duct to be treated.

SUMMARY OF THE INVENTION

The solution to this technical problem, according to the present invention, consists of an expandable tubular device for implantation in the lumen of a body duct, such as a blood vessel in particular, in order to ensure a passage therein, said device consisting of an assembly of tubular elements aligned along a common longitudinal axis and successively joined together in pairs by a plurality of linking members, each tubular element consisting of a strip forming a zigzag corrugation defining bent extreme portions which are successively connected together in pairs in opposite directions by rectilinear intermediate portions, wherein the thickness of said strip forming each of the above-mentioned tubular elements, measured radially relative to said tubular element, is greater than the width of this strip in said bent portions.

Thus, as can be seen, the novelty of the proposed solution lies in the fact that the distribution of the deformation forces during the expansion of the device is optimized by adjusting, at least in certain portions constituting each tubular element of the device, the thickness/width ratio as a function of the forces exerted thereon.

The fact that the thickness is relatively greater than the width in the above-mentioned bent portions actually makes it possible to favor a uniform expansion of the device, as it is precisely these zones which are subjected to the highest radial stresses during the inflation of the balloon.

Advantageously, to further optimize the distribution of the forces exerted on the device, both during its insertion and in the use position, the thickness of the strip forming each of the above-mentioned tubular elements will be less than the width of this strip in the rectilinear portions.

Again advantageously, the thickness of the strip constituting each tubular element is less in the rectilinear portions than in the bent portions, whereas the width of the strip constituting each of the above-mentioned tubular elements is greater in the rectilinear portions than in the bent portions.

BRIEF DESCRIPTION OF THE DRAWINGS

The invention will be better understood, and other objects, characteristics and advantages thereof will become more clearly apparent, from the following explanatory description referring to the attached schematic drawings, which are given solely by way of non-limiting examples illustrating two currently preferred embodiments of the invention, and in which:

FIG. 1 is a two-dimensional view of the evolute of the lateral surface of a device according to a first embodiment of the invention, corresponding to the constricted state of this device;

FIG. 1A is a cutaway view along the line IA—IA of FIG. 1, showing the thicknesses of the different constituent parts of the device;

FIG. 1B is a cutaway view along the line IB—IB of FIG. 1, again showing the thicknesses of the different constituent parts of the device;

FIG. 1C is an enlarged view at a bend of a portion of FIG. 1A indicated by 1C

DETAILED DESCRIPTION OF PREFERRED EMBODIMENTS

Figure 2:
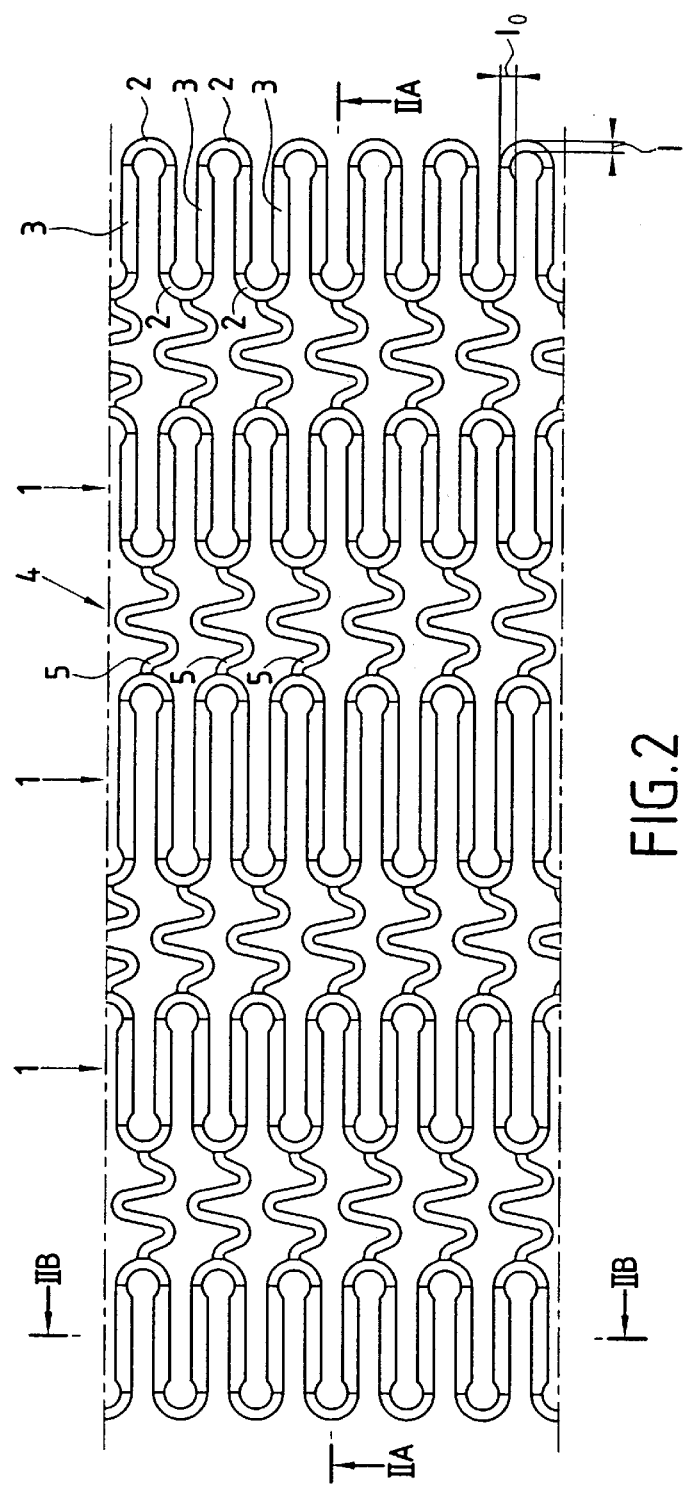
FIG. 2 is a two-dimensional view similar to FIG. 1 of a device according to a second embodiment of the invention.

FIGS. 1 and 2 therefore show an expandale tubular device according to the present invention which, for the clarity of the description, is shown in a plane configuration corresponding to the evolute of its lateral surface.

In general terms this device consists of an elongate, approximately tubular body or frame defined by a plurality of tubular elements 1 (nine in the example shown in FIG. 1 and five in the example shown in FIG. 2) aligned along a common longitudinal axis and successively joined together in pairs by a plurality of linking members, which will be described in greater detail below.

Each tubular element 1 consists of a strip forming a zigzag corrugation defining bent extreme portions 2 which are successively connected together in pairs in opposite directions by rectilinear intermediate portions 3.

Advantageously, for a given tubular element, the rectilinear portions 3 are all of the same length and the bent portions are all identical and approximately form a semicircle. Thus the above-mentioned corrugation advantageously has a uniform shape.

Figure 2A:
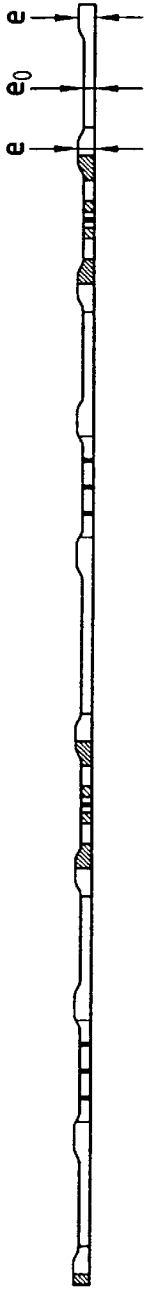
FIG. 2A is a cutaway view along the line IIA—IIA of FIG. 2, showing the thicknesses of the different constituent parts of the device.

As can be seen especially in FIGS. 1A, 1C and 2A, the thickness e of the strip forming each tubular element 1 in the bent portions 2 is greater than width 1 of this strip in said bent portions 2.

The thickness in this context is as measured radially relative to said tubular element.

As can be seen, the novelty of the present invention compared with the known state of the art lies in the fact that, in the bent portions, the device is given a particular profile (thickness greater than width) which ensures that these bent portions behave well when they are subjected to the radial forces exerted during the expansion of the tubular elements.

In the example shown in FIGS. 1, 1A and 1B, the thickness $e_0$ of the strip forming each tubular element 1 in the rectilinear portions 3 is approximately equal to the thickness e of said strip in the bent portions 2.

Advantageously, the width $1_0$ of the abovementioned strip in the rectilinear portions 3 is greater than the width 1 of said strip in the bent portions 2.

By way of example, the thickness e in the bent portions will be of the order of 0.15 mm and the width 1 of the order of 0.10 mm.

Likewise. both the thickness eo and the width $1_0$ in the rectilinear portions will be of the order of 0.15 mm.

Figure 2B:
FIG. 2B is a cutaway view along the line IIB—IIB of FIG. 2, again show in the thicknesses of the different constituent parts of the device.

In the embodiment shown in FIGS. 2, 2A and 2B, the thickness $e_0$ of the strip forming each tubular element 1 in the rectilinear portions 3 is less than the thickness e of said strip in the bent portions.

Moreover, in this case, the thickness e of the strip is greater than the width 1 as far as the bent portions 2 are concerned, whereas the thickness $e_0$ of the strip is less than the width $1_0$ as far as the rectilinear portions are concerned.

By way of example, the thickness e in the bent portions will be of the order of 0.15 mm and the width 1 of the order of 0.10 mm.

Likewise, the thickness $e_0$ in the rectilinear portions will be of the order of 0.10 mm, whereas the width $1_0$ will be of the order of 0.15 mm.

According to one particular characteristic common to both embodiments of the invention, the thickness and width transitions between the rectilinear portions 3 and the bent portions 2 will be gradual in order to avoid the formation of an incipient fracture.

The linking members which successively join the tubular elements 1 together in pairs can have a very wide variety of configurations.

In general terms these linking members will be arranged so as to be angularly spaced apart and coplanar with the tubular elements 1.

In their simplest conformation, these linking members can consist of rectilinear flat portions, as shown in FIG. 1.

Preferably, however, because of the particular conformation of the tubular elements 1, the linking members will be capable of being extended along the longitudinal axis so as to compensate for the decrease in length of the tubular elements 1 during their radial expansion, as shown in FIG. 2.

In general terms these linking members will consist of a strip, preferably of the same width as the bent portions 2, forming a zigzag corrugation also defining bent portions which are successively joined together in pairs in opposite directions by rectilinear portions.

In the currently preferred embodiment shown in FIGS. 2, 2A and 2B, the linking members designated in general terms by the reference number 4 consist of a strip forming a corrugation defining three bent intermediate portions, said linking members 4 being joined at each end to a tubular element 1 via a portion 5, which is also bent.

These linking members give the device very great bending flexibility, which makes it easier to guide it inside the vascular system by enabling the existing bends and curves to be negotiated in the best possible manner.

The device which has now been described is therefore expandable between a constricted state, enabling it to be guided inside the lumen through a body duct, such as a blood vessel, for example, and an expanded state, in which said device, after a uniform expansion, comes into contact with the inner wall of the body duct, defining a passage of approximately constant diameter inside said duct.

This device will generally be forcibly expanded mechanically under the action of a force exerted radially outwards, for example under the effect of the inflation of a balloon.

It is obvious that such a device can also be of the "auto-expandable" type, i.e. capable of changing by itself from a first, constricted position under stress, enabling it to be guided through the body duct, to a second, expanded working position.

In general terms an expandable tubular device according to the present invention can be made of any material compatible with the body duct and the body fluids with which this device may come into contact.

In the case of an auto-expandable device, it will be preferable to use a material with a recovery capacity, selected for example from the group comprising stainless steel, Phynox® and nitinol.

In the case of a device with forced expansion, a material with a low elastic recovery capacity will be used, such as, for example, a metallic material like tungsten, platinum, tantalum or gold.

In general terms a device according to the invention can be obtained from a hollow tube with an approximately constant thickness corresponding to the desired thickness of the bent portions 2.

In the case of the embodiment shown in FIGS. 1, 1A and 1B, the final configuration of the device can be obtained either by laser cutting followed by electrochemical polishing, or by chemical or electrochemical treatment.

In the case of the device shown in FIGS. 2, 2A and 2B, the desired relief can be obtained by modifying the abovementioned tube of constant thickness at the points where it is desired to reduce the thickness, i.e. at the points corresponding to the rectilinear portions 3.

The final configuration of the device can then be obtained either by laser cutting followed by electrochemical polishing, or by chemical or electrochemical treatment.

Such a device can also be obtained from a sheet of approximately constant thickness corresponding to the desired thickness of the bent portions 2.

This sheet can then be modified to reduce the thickness in the parts corresponding to the rectilinear portions 3.

The geometric configuration of the device can then be obtained either by laser cutting followed by electrochemical polishing, or by chemical or electrochemical treatment.

The sheet cut in this way is then rolled up to form a cylinder and welded to give the desired final structure.

The device which has now been described can be inserted in a manner known per se and reference may be made in this respect to the state of the art, especially document U.S. Pat. No. 4,886,062.

In the case of a device with mechanically forced expansion, the insertion system will preferably comprise a balloon-tip catheter on which the device will be positioned in the constricted state before being introduced into an insertion tube for guiding it to the site to be treated.

It should be noted that the device according to the invention can be used not only as a stent but also for the fixing of implants, particularly casings made of woven, non-woven or expanded porous polymers, or elastic membranes for the isolation of aneurisms.

What is claimed is:

1. An expandable tubular device for implantation in the lumen of the body duct in order to ensure a passage therein, said device comprising an assembly of tubular elements aligned along a common longitudinal axis and successively joined together in pairs by a plurality of linking members, each tubular element including bent extreme portions having a selected thickness and width which are successively connected together in pairs in opposite directions by rectilinear intermediate portions having a selected thickness and width, wherein the thickness of said bent portions, measured radially relative to said tubular element, is greater than the width of said bent portions wherein the width of the rectilinear portions is greater than the width of said bent portions.

2. An expandable tubular device for implantation in the lumen of the body duct in order to ensure a passage therein, said device comprising an assembly of tubular elements aligned along a common longitudinal axis and successively joined together in pairs by a plurality of linking members, each tubular element including bent extreme portions having a selected thickness and width which are successively connected together in pairs in opposite directions by rectilinear intermediate portions having a selected thickness and width, wherein the thickness of said bent portions, measured radially relative to said tubular element, is greater than the width of said bent portions wherein the thickness of the rectilinear portions is less than the width of the rectilinear portions.

* * * * *